(12) United States Patent
Ausborn et al.

(10) Patent No.: US 6,204,308 B1
(45) Date of Patent: Mar. 20, 2001

(54) ORGANIC COMPOUNDS

(75) Inventors: Michael Ausborn, Gaithersburg, MD (US); David Bodmer, Klingnau; Oskar Nagele, Sissach, both of (CH); Laurent Marchal, Mulhouse (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/260,364

(22) Filed: Mar. 1, 1999

(51) Int. Cl.$^7$ ............................ C08K 9/00; A61K 31/765
(52) U.S. Cl. .................. 523/200; 523/122; 424/78.37
(58) Field of Search .................. 523/122, 205; 424/78.37

(56) References Cited

U.S. PATENT DOCUMENTS

| | | | |
|---|---|---|---|
| 3,691,090 | 9/1972 | Kitajima et al. | 252/316 |
| 3,703,576 | 11/1972 | Kitajima et al. | 424/35 |
| 3,737,337 | 6/1973 | Schnoring et al. | 117/100 |
| 4,711,782 | 12/1987 | Okada et al. | 424/455 |
| 5,049,322 | 9/1991 | Devissaguet et al. | 264/4.1 |
| 5,407,609 | 4/1995 | Tice et al. | 264/46 |
| 5,478,564 | 12/1995 | Wantier et al. | 424/426 |

FOREIGN PATENT DOCUMENTS

| | | |
|---|---|---|
| 2 303 866 | 1/1973 | (DE). |
| 0 190 833 | 8/1986 | (EP). |
| 0 263 490 | 4/1988 | (EP). |
| 0 102 265 | 7/1992 | (EP). |
| 0 709 085 A1 | 5/1996 | (EP). |
| 2078182 A1 | 12/1995 | (ES). |
| 1394780 | 5/1972 | (GB). |
| 2 003 108 | 3/1979 | (GB). |
| 2 234 896 | 2/1991 | (GB). |
| 2 257 909A | 1/1993 | (GB). |
| 06009377 | 1/1994 | (JP). |
| 7089848 | 4/1995 | (JP). |
| 09151136 | 6/1997 | (JP). |
| 09241178 | 9/1997 | (JP). |
| 90/13361 | 11/1990 | (WO). |
| 96/22786 | 8/1996 | (WO). |
| 97/03657 | 2/1997 | (WO). |
| 97/3694 | 10/1997 | (WO). |
| 98/35654 | 8/1998 | (WO). |
| 95/13799 | 5/1999 | (WO). |

OTHER PUBLICATIONS

Furuno et al., "On the Microencapsulation of Vitamin B6 Aqueous Solution Employing (W/O/W Two–Phase Emulsion Technique," Microencapsulation Technology, vol. 5 (3), 1987, pp. 23–30.

Herrmann et al., "Biodegradable, somatostatin acetate containing microspheres prepared by various aqueous and non-aqueous solvent evaporation methods," Europ. Journal Pharm. Biopharm., vol. 45 (1), 1998, pp. 75–82.

Kawashima et al., "Properties of a peptide containing DL–lactide/glycolide copolymer nanospheres prepared by novel emulsion solvent diffusion methods," Europ. Journal Pharm. Biopharm., vol. 45 (1), 1998, pp. 41–48.

*Primary Examiner*—Kriellion Sanders
(74) *Attorney, Agent, or Firm*—Hesna J. Pfeiffer; William Kent Wissing

(57) ABSTRACT

An emulsion-based method of microencapsulating an active agent wherein a water-in-oil emulsion, containing a matrix-forming polymer and an active agent, is dispersed in an aqueous external phase to form a microencapsulated product.

9 Claims, No Drawings

ORGANIC COMPOUNDS

FIELD OF THE INVENTION

This invention is concerned with a process of microencapsulating an active agent to form a microencapsulated product, in particular a microencapsulated product containing polymers of poly(ethylenecarbonate).

BACKGROUND OF THE INVENTION

The term "microencapsulated product" as used in this specification is understood to mean a product, e.g. a microparticle or microcapsule, wherein a pharmaceutically active agent is dispersed within a polymeric matrix or is encapsulated by a polymer coating, wall or membrane. Microencapsulated products are known in the art and methods for forming said microencapsulated products may be based on emulsion technology.

Prior art processes employing emulsion-based technology may proceed by producing a water-in-oil emulsion (so-called primary emulsion) by dispersing a solution of active agent in a solution of matrix- or wall-forming polymer (Polymer) (the solvent for active agent and the solvent for the polymer (the polymer solvent) being immiscible). The primary emulsion is then dispersed in, e.g. an aqueous phase (so-called external phase) to form droplets (containing active agent-in polymer) dispersed in the external phase. The droplets so formed are then hardened by removing the polymer solvent from the droplets to form a microencapsulated product. Several methods for polymer solvent removal are known including distillation, evaporation under reduced pressure and/or heat or extracting the polymer solvent by partitioning the droplets in an extraction medium immiscible with the polymer solvent. A problem with all of these hardening steps is that they are slow and during polymer solvent removal the active agent may leach out of the droplets, resulting in poor encapsulation efficiency. By "encapsulation efficiency" is meant the measure of the amount of active substance incorporated into the microencapsulated product as a percentage of the total amount of active agent employed in a process.

In an attempt to accelerate the hardening step, it has been suggested to transfer the mixture containing the droplets to an extraction medium immediately after the mixture is formed thereby removing sufficient polymer solvent sufficiently quickly to enable the droplets to harden before a significant quantity of active agent can leach out of the droplets. Nevertheless, the need to transfer the mixture to the extraction medium immediately after the mixture is formed imposes a constraint on the process which may render it impractical and unreliable particularly when active agents are used which are highly soluble in an extraction medium.

There remains a need to provide a process of microencapsulation of an active agent to form a microencapsulated product which reliably incorporates an active agent in a polymer with high encapsulation efficiency.

Surprisingly the applicant has found that the mixture formed by mixing primary emulsion and an external phase may be dispersed to form a microencapsulated product, the microencapsulated product being formed without the need for a subsequent hardening step, i.e. a polymer solvent removal step.

SUMMARY OF THE INVENTION

Accordingly, the invention provides in one of its aspects an emulsion-based method of microencapsulating an active agent to form a microencapsulated product wherein the microencapsulated product is formed as a result of dispersing a primary emulsion, comprising or consisting of a dispersion of active agent in a solution of polymer, with an external phase.

DETAILED DESCRIPTION OF THE INVENTION

The polymer solvent used in forming the primary emulsion should be immiscible or substantially immiscible in the external phase. Preferably the polymer solvent is an organic solvent which is suitable for dissolving the polymer and which is unreactive and otherwise inert with or to the active agent, for example methylene chloride.

The external phase may be water and is preferably water when the polymer solvent is an organic solvent. However, where the polymer solvent is aqueous-based the external phase may be an organic solvent. The external phase may contain surfactants, for example suitable cationic, anionic and non-ionic compounds known in the art. Examples of suitable surfactants are gelatine or PVA, in particular PVA, preferably PVA having a molecular weight of from 5000 to 60000 Mw, in particular 15000 Mw. Other excipients may be present in the external phase, for example buffers, in particular phosphate buffers, e.g. potassium or sodium phosphates.

Surfactant, e.g. PVA may be present in the external phase in a concentration of 0.1 to 20% depending on the nature of the external phase, surfactant and polymer solvent employed. In the case of PVA the concentration preferably is, 0.5 to 5%, e.g. 2.0%. Likewise the buffer concentration is dependent upon the nature of external phase, polymer solvent and nature of the buffer. Preferably, in the case of sodium or potassium phosphate may be present in the external phase in a concentration of 20 to 100 millimolar, e.g. 60 to 70, more particularly 66 millimolar.

The polymer may be chosen from any of those polymer materials disclosed in U.S. Pat. No. 5,407,609, the contents of which is incorporated herein by reference as if set forth in its entirety. Preferred polymers are those polymers disclosed in published application WO 95/06077 which is incorporated herein by reference and in particular the poly (ethylenecarbonate) polymers disclosed therein. Preferred poly(ethylenecarbonate) polymers are those disclosed in WO 95/06077 having, e.g. a Mw of 100 000 to 800 000; and/or an ethylene carbonate content of 70 to 100% and/or an intrinsic viscosity of 0.4 to 4.0 dl/g in chloroform; and/or a glass transition temperature of 15 to 50° C.

The concentration of polymer dissolved in the polymer solvent may be 2 to 20% w/w. Preferably the polymer may be present in amounts of 10% w/w. The viscosity of the polymer solution may be 50 to 250 mPas, e.g. 240 mPas. Preferably higher viscosity polymer solutions are employed as they may contribute to producing microencapsulated product having higher encapsulation efficiency.

The active agent may be chosen from any of those active agents disclosed in U.S. Pat. No. 5,407,609. Preferably the process is used to encapsulate water soluble active agents, in particular peptides, proteins, cytokines, nucleic acids, or antibodies or viruses or parts thereof. Particularly preferred active agents are TGF-beta, Interleukins, e.g. IL-2, 3, 4, 6, 10 or 12 or, most preferably, hematopoetic growth factors, e.g. GM-CSF.

The primary emulsion may be formed by dissolving the polymer in the polymer solvent and dispersing active agent, optionally a solution of active agent, therein. Optionally the solution of polymer and the solution of the active agent may each be filtered, for example through a 0.2 micron filter before carrying out the dispersing step.

The dispersing step may be carried out using, e.g. conventional techniques and apparatus, for example turbines, static mixers, high pressure homogenisers, gear pumps or other homogenising systems using the rotor/stator principle. When, the microencapsulation process is to be carried out under aseptic conditions one may use any static mixer known in the art, however most preferred are gear pumps, e.g. an Ismatec MCP-Z gear pump.

The external phase may be formed by dissolving the surfactant and optionally any other excipients, e.g. buffers in an appropriate solvent having regard to the nature of polymer solvent. The solution thus formed may be filtered, e.g. through a 0.2 micron filter.

External phase and primary emulsion may be stored in separate tanks before mixing. Said tanks may each be equipped with pumps and flow regulating and metering equipment known in the art. Each tank may be equipped with connecting pipe work for accepting and carrying the flow of primary emulsion and external phase from their respective tanks and directing their respective flows into admixture before directing the mixture so formed onto means for dispersing the primary emulsion in the external phase (hereinafter referred to as dispersing means) described hereinbelow. In one embodiment, the pipe work of one tank may communicate with the pipe work of the other tank to permit mixing of the primary emulsion and external phase at a point before entry into the dispersing means. In an alternative embodiment, the pipe work of the tanks may not be in communication but rather may be configured as to be generally convergent at a point proximal to and directed into the dispersing means.

The rate of flow of the primary emulsion may vary widely and may depend upon, for example the rate of flow of the external phase and the capacity of the dispersing means. Preferably the flow rate is from 5 to 50 ml/minute, in particular 20 ml/minute.

Likewise the flow rate of the external phase may vary widely depending upon the flow rate of the primary emulsion and the capacity of the dispersing means. Preferably the flow rate is from 100 to 1000 ml/minute, in particular 375 ml/minute.

The flow rate of both the primary emulsion and the external phase may affect the nature of the microencapsulated product, for example the size and quality of the microparticles formed and the encapsulation efficiency. Preferably, the respective flows of primary emulsion and external phase may be chosen such that the ratio of flow rate of primary emulsion to external phase is 1:15 to 1:30.

It is an important feature of the present invention that, subsequent to mixing together the primary emulsion and the external phase, the mixture is rapidly brought into contact with the dispersing means to effect dispersion of the primary emulsion in the external phase and thereby form the microencapsulated product.

As the time elapsing between admixture of primary emulsion and external phase and dispersion of the primary emulsion in the external phase increases, so the likelihood and/or extent of extraction of polymer solvent into the external phase increases. Such extraction has the disadvantage of causing precipitation of polymer and/or extraction of the aqueous phase of the primary emulsion into the external phase, which in turn may prevent formation of microencapsulated product or affect the size and quality of the microencapsulated product and the encapsulation efficiency.

Thus, in a preferred embodiment of the present invention, the period of time elapsing between mixing and dispersing operations should be kept as short as possible. In a particularly preferred embodiment the mixing and dispersing operations may be carried out essentially simultaneously and the pipe work in relation to the dispersing means may be arranged to ensure such rapid contact of the mixture with the dispersing means. In a preferred embodiment the outlet(s) of the pipe work may be at about 1 to 2 mm distance from, e.g. the baffles of a static mixing apparatus.

Nevertheless, in the event that there may be a finite period of time between mixing and dispersing operations, the likelihood of any adverse effects associated with the incidental extraction of polymer solvent may be reduced by employing a sufficient excess of polymer solvent in the primary emulsion to take into account any loss of polymer solvent as a result of extraction into the external phase. However, the applicant has surprisingly found that it is undesirable to saturate the external phase with polymer solvent before the mixing operation in an attempt to avoid extraction. Without intending to be limited by any particular theory, the applicant believes that this is because during the dispersion step to produce microencapsulated product, the polymer solvent must rapidly diffuse into the external phase in order that the encapsulated product may harden and form in the dispersing means and such rapid diffusion may be hindered if the external phase is pre-saturated.

Dispersing means may be provided by any of the standard mixing equipment known in the art and may be, for example a turbine or static mixer. Preferably, if the process is to be carried out under aseptic conditions (in the case of a process of forming microencapsulated product containing polymers such as poly(ethylenecarbonate)s which cannot be sterilised by irradiation), it is preferable to use a static mixer.

Static mixers suitable for use in the present invention may be, e.g. any of those mixers known for use in fluid-fluid mixing. Preferred static mixers are those supplied by Sulzer and in particular Sulzer DN 3, 6 or 10 static mixers. The specifications of suitable static mixers, e.g. length, diameter and number of baffles will depend upon a number of factors including the flow rate and viscosity of the fluids passing through the mixer and may be determined by routine experimentation by a skilled addressee having regard to the foregoing discussion.

Microencapsulated product emerging from the dispersing means in a process according to the invention is distinct from the droplets formed in prior art processes described above in that the microencapsulated product comprises a coating, matrix, or wall of polymer which is sufficiently hard and self supporting that there is no need to carry out a separate hardening step, i.e. polymer solvent removal step referred to hereinabove. Optionally however, the microencapsulated product may be subjected to a further hardening step to remove any remaining polymer solvent. Said hardening step may be any of those known in the art and which have been described hereinabove. However, in a preferred embodiment any remaining polymer solvent may be removed by passing a current of $N_2$ or air over the dispersed mixture emerging from the dispersing means. The removal of the polymer solvent in this way may be facilitated by stirring the dispersed mixture collected from the dispersing means in order to drive the polymer solvent to the surface of the dispersed mixture whereupon it may be carried away on a $N_2$ or air stream.

The microencapsulated product may be worked-up according to known techniques, for example sedimentation, washing, drying and filtering steps.

The microencapsulated product may have a particle size ranging from 2 to 500 microns, e.g. 2 to 200 microns, preferably 31 microns with a standard deviation of 23 microns and may be obtained in the form of free-flowing particles.

The microencapsulated product may be obtained as microparticles or microcapsules. Whether microparticles or microcapsules are formed may be influenced by the method of forming the primary emulsion. Thus increasing shear and duration of application of shear in forming the primary emulsion may be beneficial to forming microparticles, whereas lower shear and/or shorter duration of application of shear may be beneficial to the formation of microcapsules. One can determine by routine experimentation, the desired shear force and duration to obtain microencapsulated product of choice. Preferably, the microencapsulated product is obtained in the form of microparticles.

The encapsulation efficiency of the process according to the invention may be very high, e.g. up to 92% or even greater.

The active agent loading in the case of GM-SCF may be as high as from about 2 to 3% w/w, e.g. 2.4% w/w.

The microencapsulated product may be suitable for use as a formulation for parenteral administration as well as formulations for other routes of administration, for example oral, nasal or pulmonal.

In a particularly preferred embodiment a microencapsulated product containing, for example GM-CSF as active agent and poly(ethylenecarbonate) may be used as a depot formulation for the known indications of the particular active agent incorporated therein. The amount of active agent required and the release rate thereof may be determined on the basis of known in vivo and in vitro techniques. Preferred dosage of GM-CSF in the microencapsulated product of the invention is 5 microgram per kilogram per day. The release profile of the particularly preferred embodiment and the associated advantages are described in published patent application WO 95/06077 which is incorporated herein by reference.

There now follows an example which serves to illustrate the invention.

EXAMPLE 1

A 10% polymer solution is prepared by dissolving with stirring 30 g polyethylenecarbonate (Mw 406,900) in 0.396 kg methylene chloride and filtering the solution through a 0.2 micron filter (the polymer solution). 30 ml of a 25 mg/ml aqueous GM-CSF solution is filtered through a 0.2 micron filter before being added to the polymer solution. The resultant mixture is then homogenised by passing it through a gear pump for 30 minutes to prepare the primary emulsion.

In a separate container, a 2% aqueous solution of PVA (Mw 15,000) is prepared by dissolving 400 g PVA in 20 kg of water for injection (WFI) under stirring at 80° C. The solution is then cooled to 20° C. before being filtered through a 0.2 micron filter.

The containers holding primary emulsion and the PVA solution are equipped with pumps, connecting pipe work and metering equipment. The connecting pipe work of the respective tanks converges at a point immediately above the first baffle of a static mixer. Thereby, the PVA solution and the primary emulsion are fed into said static mixer (Sulzer DN 3) at a rate of 750 ml/minute and 30 ml/minute respectively. The mixture containing encapsulated product emerging from the static mixer is collected in a vessel equipped with a stirrer and inlet and outlet ports for the ingress and egress of air or gasses. The mixture is stirred for 3 hours and a constant stream of air/$N_2$ is passed through the vessel to drive off the polymer solvent. Thereafter the encapsulated product in the form of microparticles are sedimented and the vessel is charged with WFI in order to draw off as much residual polymer solvent as possible from the microparticles. This washing step with WFI is repeated before drawing off the liquid from the vessel and charging the vessel with 20% aqueous lactose solution. The microparticles are finally freeze-dried in a lyophilizator.

We claim:

1. A method of preparing a microencapsulated pharmaceutically active agent, the method comprising the steps of
    a) dispersing an aqueous solution of a pharmaceutically active agent in a solution comprising an organic polymer solvent and a polymer dissolved therein, to form a water-in-oil primary emulsion,
    b) mixing the primary emulsion with an aqueous external phase comprising water and a surfactant; and
    c) dispersing the primary emulsion in the aqueous external phase to produce a product comprising the microencapsulated pharmaceutically active agent in a dispersed mixture,
wherein the dispersing step c is performed before the polymer solvent can be extracted from the primary emulsion as a result of performing step b, and
    d) passing a current of $N_2$ or air over the dispersed mixture.

2. The method according to claim 1 wherein the ratio of the rate of mixing the primary emulsion and the external phase is 1:15 to 1:30.

3. The method according to claim 1 wherein the active agent is GM-CSF.

4. The method according to claim 1 wherein the polymer is a poly(ethylenecarbonate).

5. A microencapsulated pharmaceutically active agent prepared according to the method of claim 1 comprising GM-CSF as the pharmaceutically active agent wherein the loading of GM-CSF is 2 to 3% w/w.

6. The microencapsulated pharmaceutically active agent according to claim 5 comprising a coating, matrix or wall of poly(ethylenecarbonate) polymer.

7. The method of claim 1 wherein the mixing step b) and the dispersing step c) are performed essentially simultaneously.

8. A microencapsulated pharmaceutically active agent prepared according to the method of claim 1 comprising GM-CSF as the pharmaceutically active agent, wherein the loading of GM-CSF is 2 to 3% w/w.

9. The microencapsulated pharmaceutically active agent according to claim 8 comprising a coating, matrix or wall of poly(ethylenecarbonate) polymer.

* * * * *